United States Patent [19]
Bingham et al.

[11] Patent Number: 6,094,599
[45] Date of Patent: *Jul. 25, 2000

[54] RF DIATHERMY AND FARADIC MUSCLE STIMULATION TREATMENT

[75] Inventors: James B. Bingham, New Braunfels, Tex.; Richard G. Olsen, Pensacola, Fla.

[73] Assignee: EHTI Medical Corporation, San Antonio, Tex.

[*] Notice: This patent issued on a continued prosecution application filed under 37 CFR 1.53(d), and is subject to the twenty year patent term provisions of 35 U.S.C. 154(a)(2).

[21] Appl. No.: 09/046,856

[22] Filed: Mar. 24, 1998

[51] Int. Cl.⁷ ..................................................... A61N 1/40
[52] U.S. Cl. ............................................................ 607/149
[58] Field of Search .................................... 607/149, 101, 607/103, 108, 109, 110, 111, 112, 154, 153, 156, 3; 600/388, 389

[56] References Cited

U.S. PATENT DOCUMENTS

| | | | |
|---|---|---|---|
| 2,583,853 | 1/1952 | Kazdin | 607/155 |
| 2,633,846 | 4/1953 | Wray | 607/111 |
| 4,305,115 | 12/1981 | Armitage | 607/154 |
| 4,368,410 | 1/1983 | Hance et al. | 318/116 |
| 4,527,550 | 7/1985 | Ruggera et al. | 128/1.5 |
| 4,685,462 | 8/1987 | Olsen | 128/422 |
| 4,791,915 | 12/1988 | Barsotti et al. | 128/24 |
| 4,873,995 | 10/1989 | Kikuchi et al. | 128/804 |
| 5,160,828 | 11/1992 | Olsen | 219/211 |

OTHER PUBLICATIONS

Olsen et al., "Rewarming of the Hyopthermic Rhesus Monkey with Electromagnetic Radiation", *Bioelectromagnetics*, 8:183–193 (1987).

Rabkin et al., "Local Heat Increases Blood Flow and Oxygen Tension in Wounds", *Arch Surg*, vol. 122, Feb. 1987, pp. 221–225.

J. Lehmann, M.D., *Rehabilitation Medicine Library*, "Therapeutic Heat and Cold", 1990, 4th Edition, 3 pp.

*Primary Examiner*—William E. Kamm
*Attorney, Agent, or Firm*—Crompton, Seager & Tufte, LLC

[57] ABSTRACT

An RF diathermy coil assembly, including a generally elastically deformable patient conforming garment and a conductive coil secured to the garment. The conductive coil having a woven wire construction such that the coil can deform as the garment elastically deforms. The RF diathermy coil assembly can be used for wound healing in conjunction with muscle stimulation.

7 Claims, 6 Drawing Sheets

RF DIATHERMY AND FARADIC MUSCLE STIMULATION TREATMENT

BACKGROUND OF THE INVENTION

This invention relates to physical medicine treatment and more specifically to RF diathermy and faradic muscle stimulation treatment for wound healing and treatment of various conditions by application of heat and/or muscle stimulation.

Applying heat to a wound has been recognized as a viable treatment for wound healing. Electrical-pulse neuromuscular stimulation has been used to aid in wound healing. In each case, it is believed that blood flow and, consequently $O_2$ flow to wound tissue is increased. Increased blood flow and thus $O_2$ flow to the wound tissue is believed to be of substantial aid in wound healing.

Resonant RF coil systems and specifically shortwave diathermy, deep-heating modality (see, Lehman, supra) can be used to provide warmth to the extremities. U.S. Pat. No. 4,527,550 to Ruggera describes a coil designed for use under full wave operation at coil wire-length resonance, designed to provide maximum muscle healing. The Ruggera coil system was operated at whatever frequency was determined to be the "resonant" frequency for the body-limb/coil combination. It would thus have to be operated within an electromagnetically shielded room in most instances in order to meet FCC noise requirements.

U.S. Pat. No. 4,685,462 to Olsen describes an apparatus for rewarming hypothermia victims. U.S. Pat. No. 5,160,828 to Olsen discloses a device for warming the extremities of a subject, such as a deep-sea diver, in a cold wet environment, so that the subject can perform agile tasks in such an environment. The Olsen coil systems were designed to be tuned to specific "Industrial-Scientific-Medical" (ISM) frequencies and, therefore, could be operated in free-space, and without shielding, without environmental interference.

The use of electrical-pulsed neuromuscular stimulation has been suggested as treatment for peripheral vascular insufficiency. See Lehman, J. F., Therapeutic Heat and Cooling, Rehabilitation Medicine Library (1990, 4th edition), p. 458; cf. U.S. Pat. No. 4,368,410 to Hance et al. (ultrasound); U.S. Pat. No. 4,791,915 to Barsotti (ultrasound). Such neuromuscular stimulation can increase the flow rates of blood and lymphatic fluid by both mechanical and electrical means. The physical contractions mechanically "squeeze" the muscles and blood vessels, and the application of electrical current pulses helps maintain the tonicity of the vessels. Although neuromuscular stimulation alone produces some beneficial effects, its effectiveness is limited.

Previously, a convenient device and method for shortwave diathermy and/or neuromuscular stimulation had not been devised to treat slow or non-healing wounds due to vascular insufficiency, diabetic peripheral neuropathy, microangiography, microvascular disease, or compression neuropathies such as Carpal Tunnel Syndrome. Furthermore, most previous and related treatment were designed for use by or under the immediate supervision of a health-care practitioner.

SUMMARY OF THE INVENTION

The present invention pertains to a device and method for wound treatment and treatment of various other conditions such as diabetic peripheral neuropathy, microangiography, osteoarthritis, microvascular disease, and/or compression neuropathies. A resonant diathermy coil system for deep heating is provided in combination with a muscle stimulator. RF heating of tissue can be accomplished in conjunction with muscle stimulation. Alternatively, either therapy, RF heating or muscle stimulation can be applied independently. The device of the present invention includes specially adapted components to accomplish the therapies as described in more detail below.

In one embodiment of the present invention, an RF diathermic coil assembly includes a primary coil. The primary coil includes a plurality of windings that are ostensibly helical and connected to a power source. The assembly also includes a secondary coil including a plurality of windings disposed proximate the primary coil. The purpose of the two coils is to provide a convenient impedance-matching method between the cable-connected power source (typically 50 ohms) and the resonant secondary coil with typical end-to-end impedance of hundreds of ohms. Therefore, the secondary coil preferably includes more windings than the primary coil. A means for tuning the body-part-plus-coil system to resonance is provided.

A means for tuning is necessary because various body parts inside a given coil system to be diathermally heated present different dielectric (capacitive) parameters and, as such, would cause the resulting resonant frequency to vary slightly. Adjusting the system to resonance can be accomplished by changing either the inductance of the coils or the capacitance of the system, most of which capacitance consists of body tissues inside the coils. Small changes in coil inductance can be made either by changing the helical length of the conductor or by changing other physical coil characteristics such as diameter or pitch. Small changes in the capacitance of the system are easily made by connecting a variable capacitor with sufficient voltage rating within the range of approximately 4 to 26 picofarads in parallel with the secondary winding. The present invention makes use of the variable capacitor. In some applications, a balun coil is added, close to the diathermic coils, in series with the coaxial cable that connects to the RF energy source. The purpose of the balun coil is to make the distribution of RF tissue warming more uniform, symmetrical, and not affected by nearby wires and/or metallic objects that share a common electrical ground with the RF energy source.

In one embodiment, the coil can be incorporated into an elastically deformable patient conforming garment. The coils are secured to the garment. The conductive portion of the coils has a woven construction such that the coils can be deformed as the garment elastically deforms. A woven RF shield can be incorporated into the garment.

An elastic wire assembly can be used to form the coils. Elastic wire assembly can include a non-conductive elastic core, a woven conductor secured to the core and a non-conductive elastic sheath over the woven conductor. The elastic core can include a plurality of polymer strands which can be deformed elastically. The non-conductive elastic sheath can include a woven fabric. The device as described herein can incorporate or be used in conjunction with a muscle stimulator for treatment of various conditions and wound healing. When used for wound healing the patient wearable garment with coil is connected to a patient. The coil is activated to heat a patient's body part to create increased blood circulation therein. Electrodes of the muscle stimulator are placed proximate to the muscles at the wounded body part. The muscles are then stimulated to increase blood circulation therein. Muscle stimulation is preferably performed while the RF coil is turned off.

DETAILED DESCRIPTION OF THE INVENTION

Figure 1:
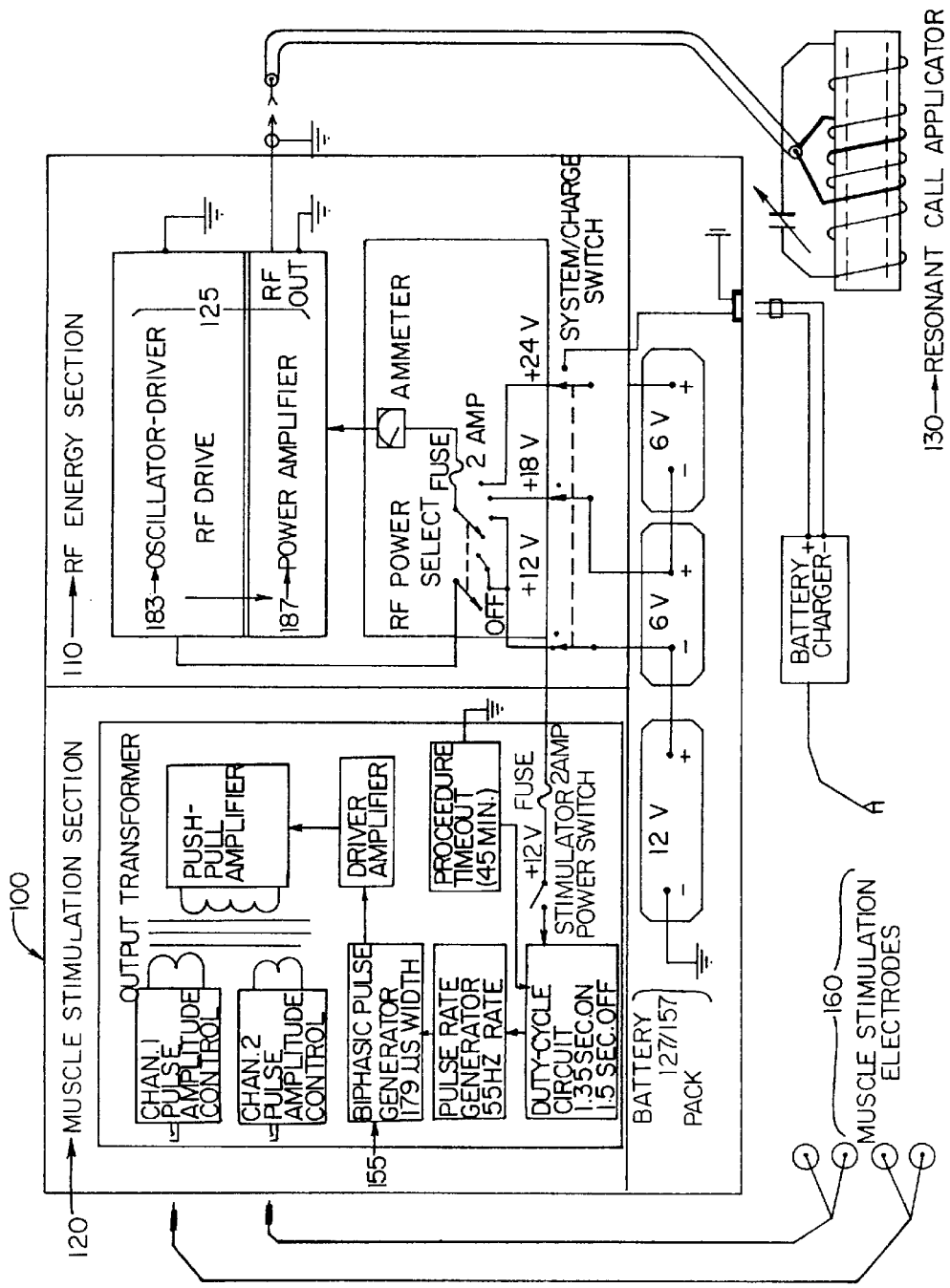
FIG. 1 is a functional block diagram of a device in accordance with the present invention.

Referring now to the drawings, wherein like numerals represent like elements throughout the several views, FIG. 1 is a block diagram of a device 100 in accordance with the present invention. Device 100 includes an RF heater portion 110 and a muscle stimulator portion 120. The RF heater portion 110 includes an RF signal generator 125 powered by a power supply 127 and a helical coil applicator 130 for insertion of a body part such as a lower leg within and for application of RF diathermal treatment to the body part. RF heater portion 110 also includes a manual on-off switch 140 and a manual power level selector control 150. Device 100 also includes a muscle stimulator portion 120 includes a muscle stimulator signal generator 155 powered by a power supply 157, at least two electrode pads 160 for application of the muscle stimulation power, and manual on-off switch 170 and a manual power level selector control 180. The RF signal generator 125 and muscle stimulator signal generator 155 can be powered by the same or different power supplies 127.

The RF heater part 110 of the device 100 is a shortwave diathermal unit for generation of deep heat within body tissues. It applies electromagnetic energy in the radio frequency bands of 13.56–40.68 Megahertz. The RF power generator circuit 125 includes an oscillator-driver 183 and a power amplifier 187. Several devices have been proposed for RF warming by Olsen. These are disclosed in U.S. Pat. No. 4,685,462 entitled "Method and Apparatus for Treatment of Hypothermia by Electromagnetic Energy", dated Aug. 11, 1987 and U.S. Pat. No. 5,160,828, entitled "Electromagnetic Warming of Submerged Extremities", dated Nov. 3, 1992 and both incorporated herein by reference.

The muscle stimulator part 120 includes two output channels, preferably having a peak current of 145 milliAmperes (mA), maximum phase change of 51.8 microCoulombs and peak power of 10 milliWatts (mW), at 500 Ohms resistance. The waveform is preferably biphasic and symmetrical. The frequency of the wave is preferably 55 Hz and the on-off timing is about 1.3 sec on and about 1.5 sec off. The muscle stimulator 120 is operated by direct application of voltage to the skin by means of electrode pads 160. The stimulator has an automatic shutoff timer 190 which shuts it down after about 45 minutes. A buzzer will sound if the patient/operator has failed to turn off the switch 170 by this time. Usually, the warming unit 110 and the muscle stimulator 120 will not operate at the same time due to electromagnetic interference between the two portions 110 and 120.

The following table lists exemplary characteristics of the device 100.

| Control Unit 190 | |
| --- | --- |
| Size (W × D × H): | 7.5" × 4.5" × 2.75" |
| Weight: | 11 lbs. |
| RF Heater Part 110 | |
| Frequency: | 27.12 MHz |
| Wavelength: | 11.06 meters |
| Mode: | continuous |
| Output Power: | 8–24 Watts |
| Applicator 130: | helical coil |
| Turning to Resonance: | manual |
| Power Control: | manual |
| Power Consumption: | 28 Watts operating; 50 VA charging |
| Energy Course 127: | Rechargeable battery, 12–24 Volts DC, in 6 V gradations |
| Specific Absorption Rate ("SAR"): | minimum 1 W/kg; maximum 4 W/kg |
| Cooling: | heat sink |
| Fuse 195: | Yes |
| Muscle Stimulator Part 120 | |
| Waveform: | Bi-phasic |
| Description: | Symmetrical, Balanced, Spiked |
| Current: | 0–250 mA |
| Power Source 127: | Rechargeable batteries; 12 & 6 Volts DC |
| Maximum Phase Charge: | 51.8 microCoulombs ($\mu$ C) 25.9 $\mu$ C per phase at 500 Ohms $\Omega$ |
| Peak Amplitude: | 90 V baseline to peak |
| Duty Cycle: | 1.3 sec. on; 1.5 sec. off |
| Frequency: | 55 Hz. |

All of the above described values are exemplary and may be varied without departing from the spirit or scope of the invention. For example, the RF power may be 8 watts for light individuals or 24 watts for heavier patients.

Figure 2:
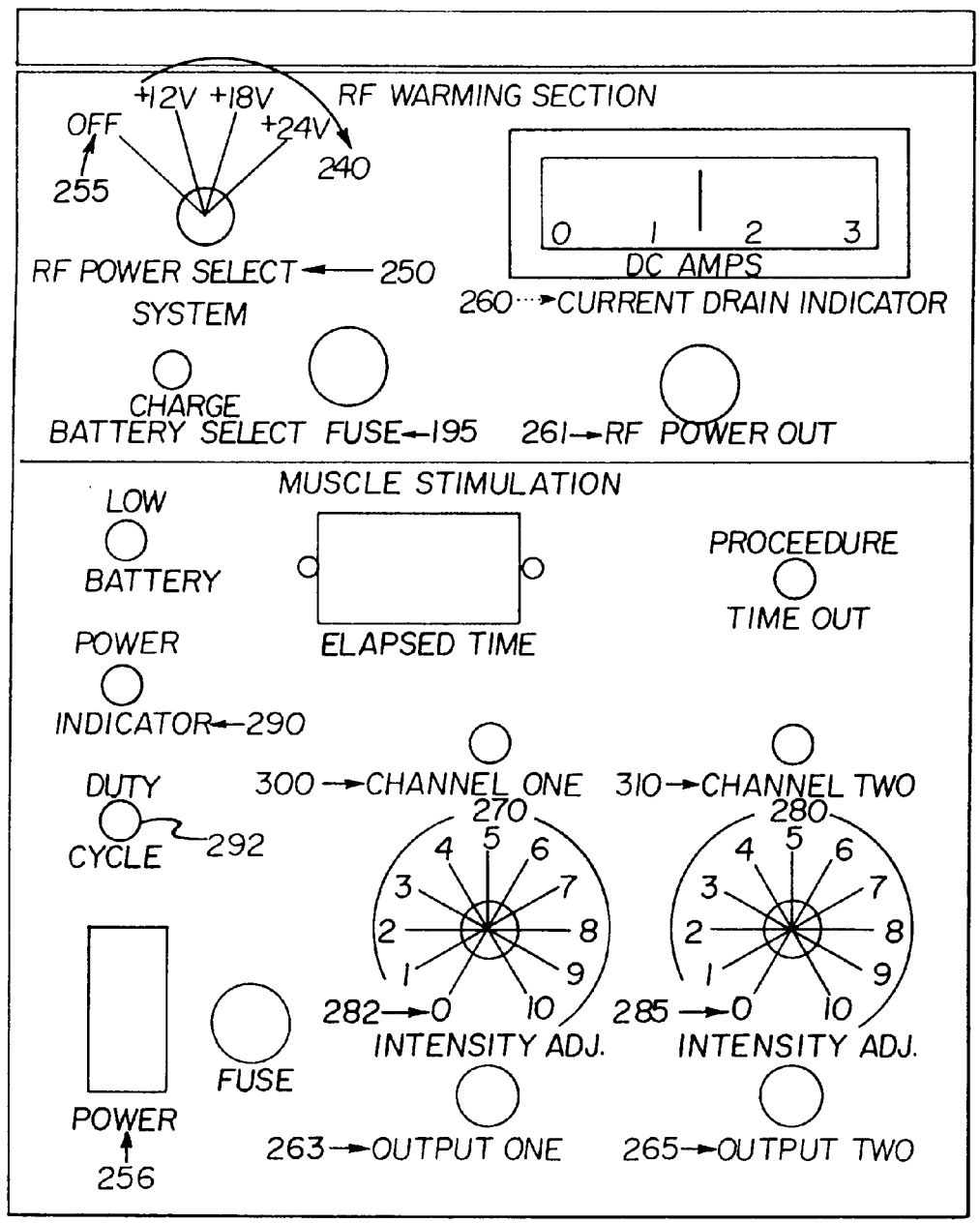
FIG. 2 is a drawing of the control panel for the device in accordance with the present invention.

FIG. 2 is a view of a control panel 190 for device 100. Control panel 190 includes an assortment of switches, indicators, knobs, and other surface hardware labeled as to function. The device 100 limits the power by controlling voltage. Voltage can be selected by select switch 250. The three power levels of the RF heating unit 110 (12 V, 18 V, 24 V) are clearly indicated by labels 240. Power off is indicated by label 255. A current drain meter 260 indicates the amplitude of the electrical current flowing to the RF unit. All energy output ports are clearly marked on the control panel 190. RF power is output to line 261.

Thee muscle stimulation portion 120 has labeling on the control panel 190 indicating two output channels 263 and 265 with intensity setting 1–10 in increments of 1, set by controls 270 and 280, respectively, and turned on or off by on-off switches 282 and 285, respectively. Exemplary equivalent power density at each intensity setting is described in the following table:

| Intensity Setting | Power Density Microwatts/Sq. Cm. |
| --- | --- |
| 1 | 86 |
| 2 | 172 |
| 3 | 258 |
| 4 | 344 |
| 5 | 430 |
| 6 | 516 |
| 7 | 602 |
| 8 | 688 |

-continued

| Intensity Setting | Power Density Microwatts/Sq. Cm. |
|---|---|
| 9 | 744 |
| 10 | 860 |

A labeled light emitting diode 290 is used to indicate that the power is on (red) and green LEDs 300 and 310 indicates when the pulse train is on for channels one or two, respectively. A power off/on switch 256 for stimulator part 120 is disposed at the lower left. The following is a listing of remaining switches, gauges, input/output ports, etc. of control panel 190: fuse(s) 195, muscle stimulator Channel 1 output jack 263, muscle stimulator Channel 2 output jack 265. The duty cycle indicator is a blinking yellow light 292 located above muscle stimulator power switch 256; it indicates when electrical current is flowing through the stimulator. The muscle stimulator part 120 utilized high voltage medical-grade cables with ¼" phone plugs for the outlet channels and with carbon rubber electrodes, both the cables and electrodes being obtained from Bloomex Medical Corp, 295 Molnar Drive, Elmswood Park, N.J. 07407-3211. The device is suitable for application to various anatomical sites, including, but not limited to, lower legs, feet, joints, hands and knees.

Figure 3:
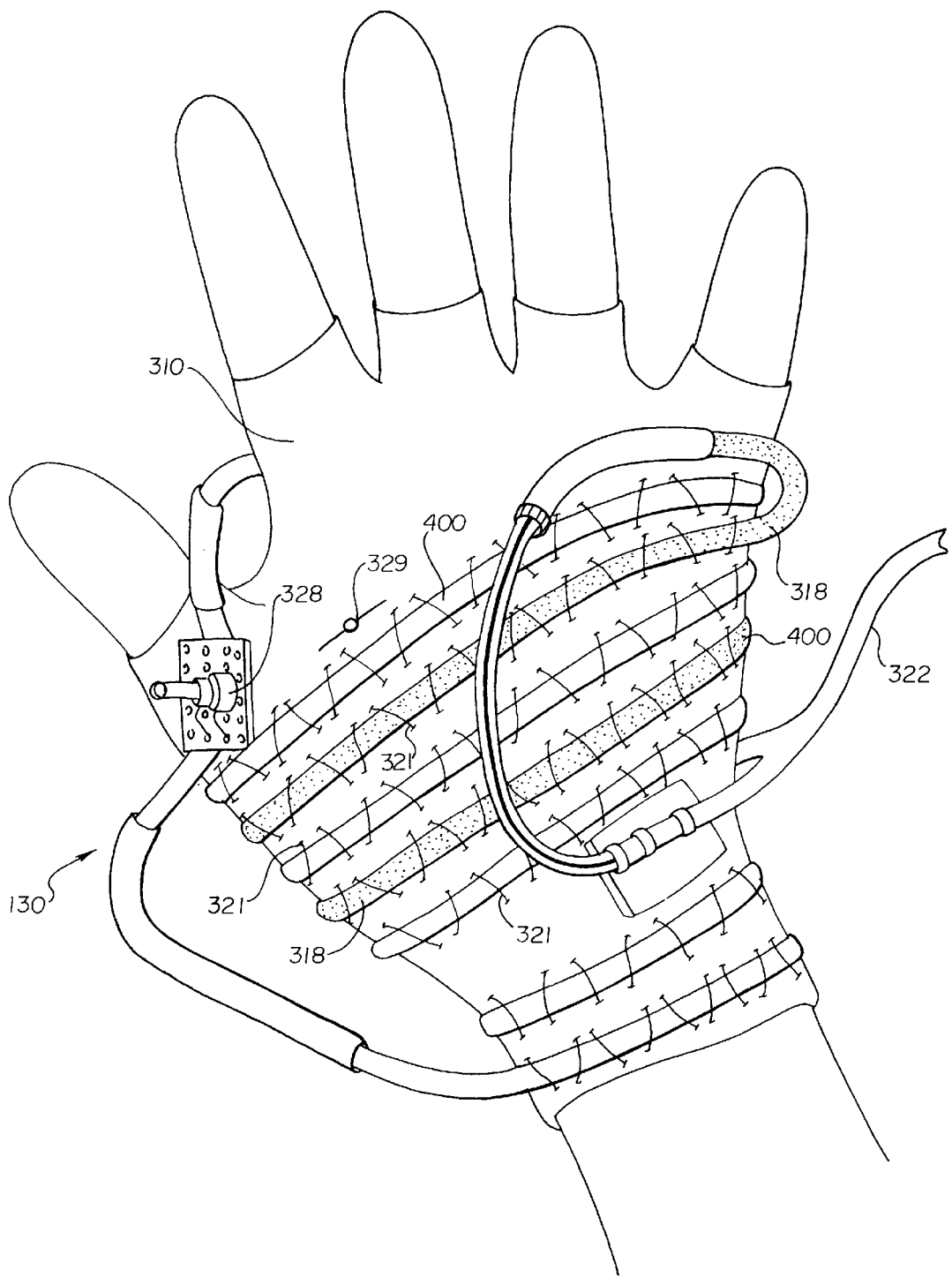
FIG. 3 is a drawing of an RF coil assembly in accordance with the present invention.

FIG. 3 is a schematic view of an RF diathermy coil assembly 130 in accordance with the present invention. Coil assembly 130 includes a patient wearable garment 310, such as a glove. A patient's hand can be placed within glove 310. Preferably, glove 310 is formed from a flexible, elastically-deformable material such that the glove can be sized to snuggly, yet not restrictively fit to a patient's hand. Primary coil 318 and secondary coil 320 are affixed to glove 310 by fasteners 321. Thread, staples, glue or other fasteners which would allow glove 310 to elastically deform can be used to fasten coils 318 and 320 to glove 310.

Primary coil 318 can be connected to R signal generator 125 by lead 322. Coil assembly 130 can include a tuning device for adjusting the RF frequency passing through coils 318 and 320. The tuning device preferably includes a tuning capacitor 328 connected to secondary coil 320 and an LED 329 disposed adjacent a coil. Tuning capacitor can be adjusted until LED 329 appears its relative brightest. At that point, the RF frequency will be roughly the resonant frequency of the patient's hand within glove 310. This frequency is preferably the resonant frequency of the nearest ISM frequency. Primary and secondary coils 318 and 320 can be formed from an elastic wire 400 described in more detail below with respect to FIG. 5. Elastic wire 400 allows the wrist portion of glove 310 to stretch over the palm of the patient as glove 310 is placed on the patient's hand. Elastic wire 400 will then elastically rebound to be snug around the patient's wrist. Glove 310 and coils 318 and 320 can be sized such that in view of the elastic character of glove 310 and wires 400, a snug positive fit between the patient's hand and glove 310 can be achieved.

Figure 4:
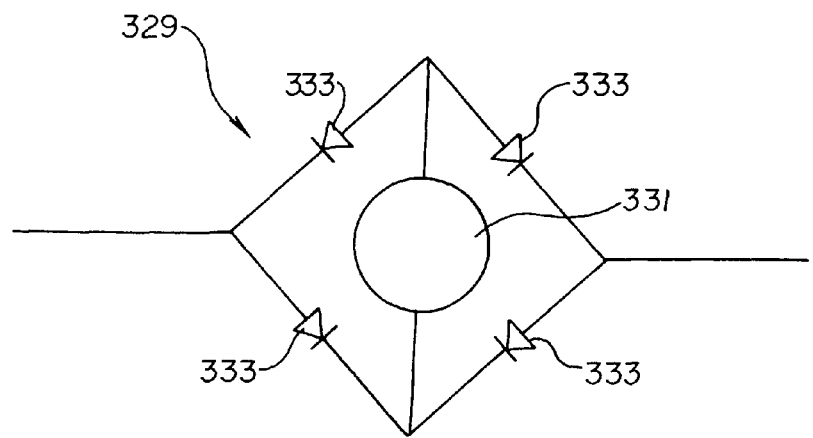
FIG. 4 is a light emitting diode (LED) circuit for tuning the RF coil assembly.

FIG. 4 is a typical LED assembly 329 which includes an LED 331 having four bridge rectifiers 333. In reality, assembly 329 can be directly connected to a coil, but as discussed previously, need merely be placed against a coil in the RF field to be functional. The RF field will be closest to resonant frequency when the LED is at its brightest under the influence of the field.

Figure 5:
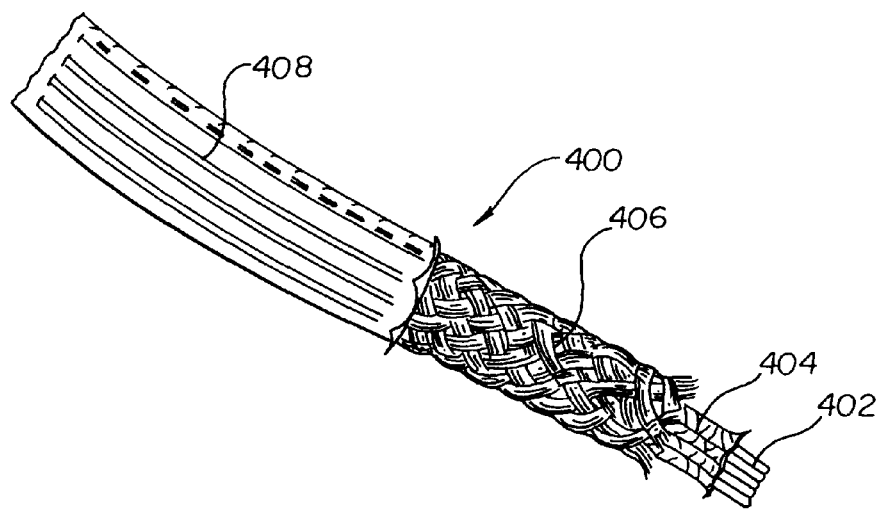
FIG. 5 is a drawing of an elastic wire in accordance with the present invention.

FIG. 5 is a drawing of an elastic wire 400 in accordance with the present invention. As shown, elastic wire 400 includes a plurality of elastic polymer filaments 402 surrounded by a woven insulative sheath 404. A woven conductive member 406 surround sheath 404 and an insulative cover 408 surrounds conductor 406. Each of the woven members 404, 406 and 408 can have a weave pattern similar to that shown for conductive member 406. As such, these members can be elongated when placed under longitudinal stress. Sufficient mechanical connection should be made between the woven layers and the elastic filament 402 that if elastic wire 400 is placed under stress, it will elongate, and when the stress is relieved, it will shorten as the elastic filaments 402 shorten. Elastic filaments may be woven into member 404 and 406 to increase the elastic rebound of elastic wire 400 when stress is removed from the wire. In one embodiment, wire 400 can stretch elastically approximately 30% of its relaxed length. If the wire is used to form a coil, the diameter of the coil can decrease approximately 10% when the wire elongates approximately 30%, the electrical conductivity of the coil remains constant.

Figure 6A:
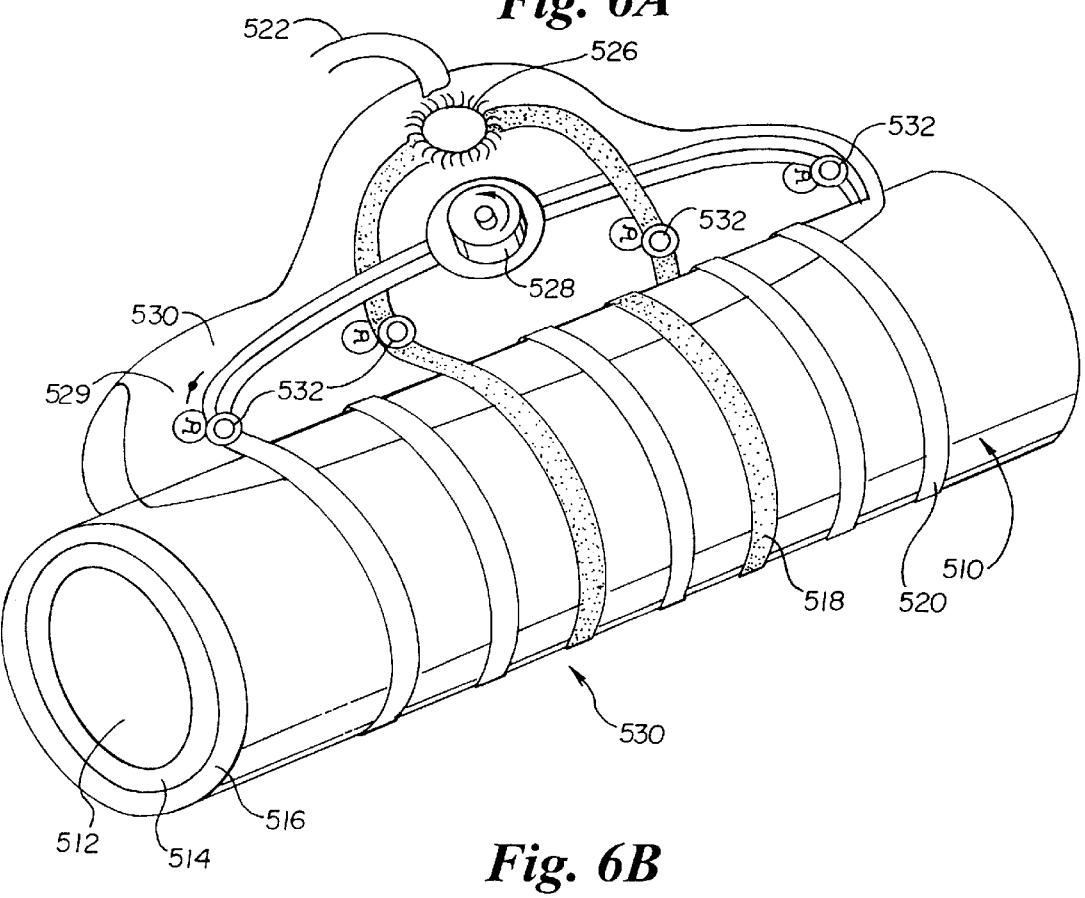
FIG. 6A is a schematic drawing of an alternative RF coil assembly in accordance with the present invention.

FIG. 6A is a schematic view of an alternate embodiment of the RF diathermy coil assembly 530 in accordance with the present invention. Assembly 530 includes a patient wearable garment 510. Garment 510 as shown in FIG. 6A is substantially tubular shaped and hollow including passage 512 therethrough. A patient limb of body part can be placed within passage 512. Preferably garment 510 is formed from a flexible elastically deformable material such as a polymer foam. The transverse cross section of passage 512 in garment's 510 relaxed state is preferably slightly larger than the transverse cross section of a patient body part placed therein such that garment 510 will have a slightly snug fit on the patient body part.

Garment 510 as shown in FIG. 6A is formed from two layers of fabric 514 and 516. Sandwiched between layers 514 and 516 is a primary coil 518 and a secondary coil 520 (primary coil 518 is shown shaded to contrast it from secondary coil 520). Primary coil 518 is connected to RF signal generator 525 by lead 522.

Coil assembly 530 preferably includes a tuning device which enables the RF frequency passing through coils 518 and 520 to be tuned to the resonant frequency of the body part disposed within passage 512 of garment 510. The tuning device can include a balun 526 connected to primary coil 518 and a tuning capacitor 528 connected to secondary coil 520. An LED 529 can be connected to secondary coil 520. When in use, tuning capacitor 528 can be adjusted until LED 529 appears it's relative brightest. The balun can be used where space is available and power is relatively high.

Balun 526 and tuning capacitor 528 can be placed within a housing 530 shown in FIG. 6A. Housing 530 can be releasably connected to coils 518 and 520 by fasteners 532. Fasteners 532 are a snap-type fastener. Any of several conductive releasable fasteners, however, could be used. Releasably coupling housing 530 to coils 518 and 520 is a particularly advantageous feature as will be explained in more detail below as garments such as garment 510 can be configured in numerous manners to accommodate various patient body parts and disposable coil assemblies.

Figure 6B:
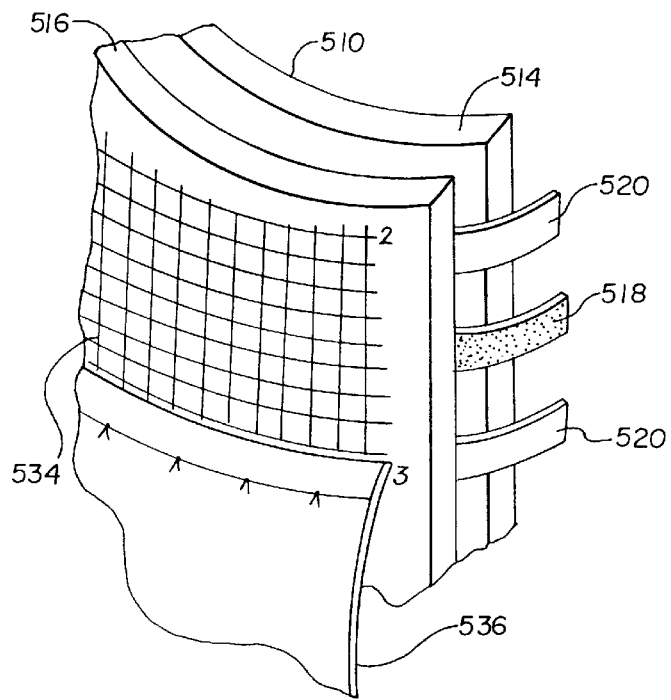
FIG. 6B is a partial, cross-sectional portion of the schematically represented RF coil assembly of FIG. 3A.

FIG. 6B is a partial, cross-sectional portion of the schematically represented RF coil assembly of FIG. 6A. FIG. 6B shows coils 518 and 520 sandwiched between layers 514 and 516. Disposed to the outside of layer 516 is an RF shield 534. RF shield 534 may be, for example, a steel screen such as the fabric used to make window screens. Shield 534 can be protected from abrasion or snagging by covering 536 shown pulled partially away from layer 516 to reveal shield 534.

Figure 7:
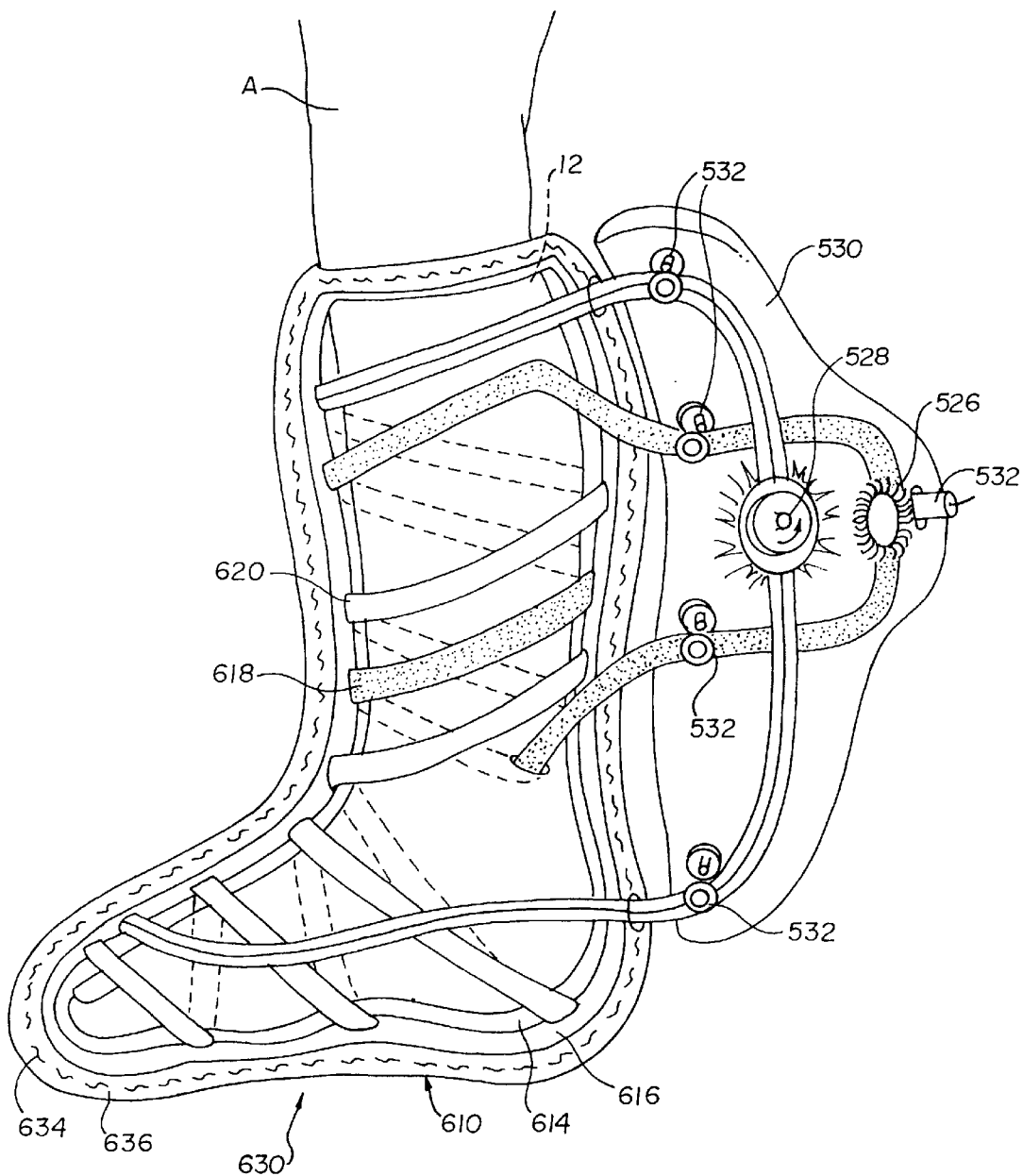
FIG. 7 is a cross-sectional, schematic drawing of an alternate RF coil assembly for foot/ankle applications.

FIG. 7 is a cross-sectional, schematic view of a coil assembly 630 for a calf, foot and ankle A. Similarly to the coil assembly of FIG. 6A, the coil assembly of FIG. 7 includes a wearable garment 610 defining an opening for the calf, foot and ankle A of a patient. A primary coil 618 and a secondary coil 620 are sandwiched between layers 614 and 616. An RF shield 634 is disposed outwardly from layer 616. Shield 634 can be protected from abrasion or snagging by cover 636.

Housing 530, including balun 526, tuning capacitor 528 and lead 532 can be releasably coupled to the coil assembly of FIG. 7 by fasteners 532 as described above. It can be appreciated that the coil assembly garment can be configured as in FIG. 6A or as configured FIG. 7, as well as in several other configurations such as a glove to fit various body parts. The housing and related components, however, need not vary in configuration but can be releasably fastened to any of the garments.

In use, for wound healing, a tissue of the patient which tissue is to be treated is identified. The tissue can include skin, a muscle and a nerve vascular bed. The tissue is heated by RF diathermy for a period of time, for example, about 10–30 minutes, preferably to a maximum of 40° C. That heating induces vasodilation oxygen perfusion to at least a portion of the tissue. After the RF diathermy heating, muscle stimulation increases oxygen delivery and increase the flow of previously warmed blood to the tissue. Muscle stimulation continues for an exemplary period of usually less than 45 minutes and preferably for a period of from 10–30 minutes.

Because of the consequential increased oxygen and blood perfusion, the RF heating better prepares the muscle for muscular contraction, and makes it less likely that the muscle contractions will cause soreness, cramping or irritation. Thus, the RF heating before the muscular stimulation enhances the safety of this treatment, which is an especially important feature because the subjects of this treatment are often elderly or have severe muscular atrophy. It should be noted that for wound healing, a beneficial effect is expected from RF heating or muscle stimulation together as described above or independently.

The device 100 is designed for home use directly by the patient without the immediate supervision of a health-case practitioner. As to the RF diathermy, the device uses a rechargeable battery 127, thus minimizing the risk of electrocution. Individuals not undergoing treatment should stay outside of a 1 meter range while the RF heating unit is on. Fuses are used in the device 100 to protect against short circuits and component failure. The energy used by the RF signal generator 125 is controlled through the power source 127 by limiting voltage which can be varied from 12 V to 24 V by a power switch 140. The helical coil applicator 130 will deliver energy in longitudinal electrical fields with respect to the limb. The helical coil 130 is approximately five turns with about 7 foot of coil length.

The level of deep heating for the patient using the device 100 will not exceed 3° C. above normothermic temperature. The level of deep heating for the patient using the device 100 is controlled by the setting of the power level selected control 150. The RF heater part 110 is tuned to resonance by a tuning capacitor which the patient will tune to the brightest level of a light emitting diode LED located near the tuning capacitor. The resonance tuning is preferably first performed at a low level of power, before the actual therapeutic level is set. The capacitor adjustment is to be monitored during the treatment so that it remains at the brightest level. Keeping the RF diathenny unit 110 in resonance (by adjusting the capacitor rather than adjusting the operating frequency) keeps the warming at optimal efficiency in terms of energy in/energy out in the firm of body warming capability.

The device 100 delivers energy instantly, with a subsequent thermal rise occurring primarily throughout the muscle. In general, fat and bone are heated at a much lower rate than muscle. The RF unit 110 uses a fixed radiofrequency circuit 125 with 11.06 meter waves and 27.12 MHz frequency. A high efficiency RF source is used with minimal loss of power and maximal energy delivered. Due to the nature of this heating method and the limitation of power from the energy source 127, there is little likelihood of overheating and/or skin burns. The tuning of the RF circuit (including the coil 130) into resonance is influenced by the composition of fat, muscle, and bone of the patient's limb, and generally varies from patient to patient.

As to muscle stimulation, the unit is fused for prevention of surging. The device is heat-sinked so that it does not overheat; it has two output circuits (or channels) that are variable in amplitude. The muscle stimulator unit's power cannot be activated until both channels are set on "0" when the device is turned on. Furthermore, as shown in FIG. 1, the muscle stimulator will not work while the battery 127 is being charged.

Heating by the RF diathermy step of this regime occurs throughout all tissues of the limb; therefore, certain perfusion-reducing affects are prevented such as that of excessive arteriovenous (AV) shunting of blood that might occur in diabetic neuropathy patients who are treated with surface-only warming. With total-tissue warming, the core vasculature is dilated thus increasing oxygen perfusion to the endoneurium (nerve capillary bed) and improving neural function.

The RF heating portion of the diabetic neuropathy regime is preferably done over a period of generally less than about forty-five minutes. Alternately, the leg of the subject could be inserted in a leg coil of a heating element at night and worn during sleep, when flow rates are lowest, provided that body movement during sleep should somehow be restricted so as to prevent the patient from being entangled in the RF cable. The RF heating apparatus would be automatically turned on and off intermittently during the night and, ostensibly, prevent stasis and hypoxia during this low blood flow rate danger period.

For lower extremity treatment, the lower leg is placed inside helical coil 130. It is recommended that the patient be seated or lying down and not be standing during the RF diathermy and muscle stimulation treatment application. All metallic jewelry should be removed from the part of the tissue being treated. The on-off switch 140 is turned on and the level control 150 is set to one of the three available power levels closest to the prescribed power level. The leg is warmed by the RF diathermy part 110 for 25 minutes. The on-off switch 140 is turned off. The electrode pads 160 of the muscle stimulator component 120 are placed on the following muscles of the leg being treated: tibialis anterior, vastus lateralis, soleus, and rectus femoris. For use of carbon rubber electrodes 160, the electrodes 160 are fastened on the patient with Velcro pads so as to hold the electrodes 160 firmly against the patient's skin. The electrode pads 160 are thoroughly wetted with salt water (the precise concentration of sodium is not important), and the electrodes 160 are checked for the absence of oil. If the salt water beads up on the black electrode surface, then there is oil on it. The electrodes 160 should then be thoroughly scrubbed with a mild abrasive cleaner and a scrub brush, until water no longer beads on the surface. New electrodes 160 may have to be washed several times to remove the oil. If the electrode pads dry out during the course of a treatment, they should be rewetted.

The on-off switch 170 is turned on and the level control 180 is adjusted to a level sufficient to make the muscles visibly contract. The muscles are contracted for 25 minutes. The electrodes 160 may be shifted and repositioned during the course of a treatment. If they are partially pulled away from the surface of the skin while current is flowing, the patient may feel a sharp tingling sensation. Therefore, the output channel should be turned off to reposition or rewet the electrodes 160. After muscle stimulation treatment is concluded, the on-off switch 170 is turned off and the electrode pads 160 are removed from the leg.

Another type of electrode 160 that might be used is self-adhesing gel pads 160. Always clean the skin with alcohol before applying these electrodes 160. Place the electrodes 160 firmly on the dry skin.

The protocol for treatment of a hand having Carpal Tunnel Syndrome includes placing the glove applicator on the hand to be treated. The on-off switch 140 is turned on and the level control 150 is set to the power level prescribed by a physician. The hand or hands is or are warmed by the RF diathermy part 110 for 25 minutes. The on-off switch 140 is turned off. The electrode pads 160 of the muscle stimulator component 120 are placed on the following muscles of the hand or hands and forearm or forearms being treated: flexor carpi unlaris, palmaris, pronator quadratus, lumbricals, palmarand dorsal interossei, pollicis brevis, palmaris brevis, and digiti minimi brevis. The on-off switch 170 is turned on and the level control 180 is adjusted to a level sufficient to make the muscles visibly contract. The muscles are contracted for 25 minutes. The on-off switch 170 is turned off. The heating muscle stimulation process can be repeated as necessary.

In addition to heating for wound healing, diabetic neuropathy and Carpal Tunnel Syndrome, heating may also be preformed for treatment of Raynaud's disease. In such a case, a form of a coil assembly such as that shown in FIG. 3 would be used to warm the Raynaud's patients' fingers which often feel cold.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An RF diathermy coil, comprising:
    a generally elastically deformable patient-conforming garment; and
    a conductive coil secured to the garment, the conductive coil having a woven wire construction such that the coil can be deformed as the garment elastically deforms.

2. The RF diathermy coil assembly in accordance with claim 1, further comprising a woven RF shield connected to the garment, wherein the shield is disposed toward the exterior of the garment relative to the majority of the length of the coil.

3. The RF diathermy coil assembly in accordance with claim 1, wherein the conductive coil further comprises a non-conductive elastic deformable core.

4. The RF diathermy coil assembly in accordance with claim 3, wherein the elastic core includes a plurality of polymer strands which can form elastically.

5. The RF diathermy coil assembly in accordance with claim 1, wherein the coil further comprises a non-conductive elastically deformable sheath over the woven wire.

6. The RF diathermy coil assembly in accordance with claim 5, wherein the non-conductive sheath includes a woven fabric.

7. The RF diathermy coil assembly in accordance with claim 1, wherein the garment includes a polymer foam.

* * * * *

UNITED STATES PATENT AND TRADEMARK OFFICE
CERTIFICATE OF CORRECTION

PATENT NO.    : 6,094,599
DATED         : July 25, 2000
INVENTOR(S)   : Bingham et al.

It is certified that error appears in the above-identified patent and that said Letters Patent is hereby corrected as shown below:

<u>Title page,</u>
Item [73], Assignee, please insert -- The United States of America as represented by the Secretary of the Navy, Washington, DC -- after the current listing noting the 1st assignee.

Signed and Sealed this

Ninth Day of July, 2002

*Attest:*

*Attesting Officer*

JAMES E. ROGAN
*Director of the United States Patent and Trademark Office*